United States Patent [19]
Nishinaka et al.

[11] Patent Number: 5,849,539
[45] Date of Patent: Dec. 15, 1998

[54] THYMIDINE KINASE-LACKING OUABAIN-RESISTANT CHICKEN HYBRIDOMA

[75] Inventors: Shigeyuki Nishinaka, Hyogo; Hisaya Akiba, Saitama; Yasuko Yao, Tokyo, all of Japan

[73] Assignee: NKK Corporation, Tokyo, Japan

[21] Appl. No.: 631,571

[22] Filed: Apr. 12, 1996

[30] Foreign Application Priority Data

Apr. 14, 1995 [JP] Japan ................................ 7-088950

[51] Int. Cl.⁶ .............................. C12N 5/12; C07K 16/00
[52] U.S. Cl. .................. 435/70.2; 435/70.21; 435/172.2; 435/326; 435/346; 435/349
[58] Field of Search .............................. 435/70.21, 240.2, 435/240.27, 70.2, 172.2, 326, 346, 349

[56] References Cited

U.S. PATENT DOCUMENTS 5,411,881  5/1995  Matsuda et al. ................... 435/240.27

FOREIGN PATENT DOCUMENTS 148 644  7/1985  European Pat. Off. .
491 057  6/1992  European Pat. Off. .

OTHER PUBLICATIONS

Somatic Cell and Molecular Genetics, vol. 14, No. 3, 1988, pp. 305–314, Zinkewich–Peotti, K. et al, "Development and Characterization of Mutant Chicken Cell Lines . . . ".

Immunology Letters, vol. 32, 1992, pp. 91–96, Asaoka H. et al, "Two chicken monoclonal antibodies specific for heterophil Hanganutziu–Deicher antigens".

Journal of Immunological Methods, vol. 139, 1991, pp. 217–222, Nishinaka S. et al., "A new cell line for the production of chicken monoclonal antibody hybridoma technology".

Kozbor et al Human hybrodomas constructed with antigen–specific Epstein–Barr virus–transformed cell lines Nat'l Acad. of Science USA vol. 79 pp. 6651–6655 Nov. 1982.

Campbell, A Monoclonal Antibody Technology 1984 pp. 73–75.

Langone, J et al., Immunochemical Techniques, Part I 1986 pp. 152–153.

*Primary Examiner*—Lila Feisee
*Assistant Examiner*—Nancy A. Johnson
*Attorney, Agent, or Firm*—Flynn, Thiel, Boutell & Tanis, P.C.

[57] ABSTRACT

The thymidine kinase-lacking hybridoma of the invention has resistance to oaubain and an Ig-producing ability and is formed by fusing a chicken B lymphoblast cell with an immunized chicken spleen cell. The hybridoma can be used as parental cell line for cell fusion, and the fused cell is excellent in the production of IgG.

4 Claims, 4 Drawing Sheets

FIG. I

DETECTION OF IMMUNOGLOBULIN PRODUCED BY
MuH1, MuH4 CELL

LANE 1: MuH11
LANE 2: MuH44

DETECTED ANTIBODY a: MOUSE MONOCLONAL ANTIBODY AGAINST CHICKEN L CHAIN
b: MOUSE MONOCLONAL ANTIBODY AGAINST CHICKEN $\mu$ CHAIN
c: MOUSE MONOCLONAL ANTIBODY AGAINST CHICKEN $\tau$ CHAIN TITER OF CHICKEN SERUM IMMUNIZED WITH HUMAN IgG BEFORE IMMUNIZATION (O)
AFTER 14TH DAY FROM FIRST IMMUNIZATION (□)
AFTER 3RD DAY FROM SECOND IMMUNIZATION (△)

SPECIFICITY OF CHICKEN MONOCLONAL ANTIBODY

10% SDS-PAGE
NONREDUCING

LANE 1: HUMAN IgG-Fc
LANE 2: HUMAN IgG-Fab a: CONTROL (ANTIHUMAN IgG ANTIBODY)
b: CHM1-HuIg1 CULTURE SUPERNATANT
c: CHM1-HuIg3 CULTURE SUPERNATANT
d: CHM4-HuIg1 CULTURE SUPERNATANT

THYMIDINE KINASE-LACKING OUABAIN-RESISTANT CHICKEN HYBRIDOMA

BACKGROUND OF THE INVENTION

This invention relates to an established hybrid cell having an IgG-producing ability obtained from a chicken, its preparation method, and a method of producing an antibody utilizing this hybrid cell.

It is known that chicken-immunized globulin IgG has a very low cross-reactivity with IgG derived from a mammal (Hadge, D., et al, Mol. Immunol., 21, 699–707, 1984). Moreover, it is also known that the chicken IgG does not bind protein A (Guss, B. et al, EMBO J., 5, 1567–1575, 1986). Furthermore, the chicken antibodies have the advantages of not activating the complement system and not reacting with the rheumatoid factor in mammalian sera (Larsson, A., et al, I. Immunol. Methods, 108, 205–208, 1988). Thereupon, an assay for measuring circulating immune complexes using a chicken anti-human complement antibody has recently been established (Largson, A., et al, J. Immunol. Methods, 113, 93–99, 1988). These facts indicate that chicken antibody is extremely useful in mammalian immunology field. Therefore, it is considered that, if a chicken monoclonal antibody can be supplied, the antibody can be utilized as a useful means not only in the field of avian immunology but also in that of mammalian immunology.

The present inventors eagerly investigated in order to establish a parental cell line for the preparation of a chicken monoclonal antibody, and examined to produce a cell line lacking an enzyme necessary for selection of hybridomas from chicken B cells, similar to a mouse myeloma cell. As a result, we obtained a cell which can grow stably among thioguanine-resistant cells. However, all of the thioguanine-resistant cells have HAT (hypoxanthine-aminopterin-thymidine) resistance. Thereupon, we further investigated, and as a result, we established a thymidine kinase-lacking cell line with HAT sensitivity (HU3R cell line) which can stably multiply. Thus, we found that, when the established cell was fused with an immunized chicken spleen cell, a chicken monoclonal antibody could be accumulated in a culture medium by culturing the fused cell (the specification of Japanese patent KOKAI No. 2-186980, Int. Arch. Allergy Appl. Immunol., 88, 416–419 (1989)).

However, antibodies produced by the hybridoma formed by fusing the HU3R cells are not IgG but IgM, and moreover, the cells lost the antibody-producing ability rapidly during sub culturing.

Then, we further investigated, and obtained thymidine kinase-lacking cells (R27H cell line) from the above hybridoma. The thymidine kinase-lacking cells were fused with chicken spleen cells immunized with an antigen to produce novel hybridomas (J. Immunol. Methods, 139, 217–222, 1991, U.S. Pat. No. 5,411,881). As a result, it became possible to obtain hybridomas which could produce a specific antibody stably, and several chicken monoclonal antibodies were produced by using the hybridomas and applications thereof were reported (Animal Cell Technology: Basic & Applied Aspects, 527–534, 1992, Immunology Letters, 32, 91–96, 1992).

However, multiplication of cells, which had been transformed by chicken retroviruses carried by the parental chicken B cells, frequently occurred during fusions with the R27H cells and were capable of growing in a in HAT medium which resulted in the difficulty of the multiplication of only hybridomas formed through the fusion selectively. That is, the cells transformed by retroviruses can multiply in a HAT medium, and the growth rate of the cells is greater than the hybridomas. The appearance frequency of the cells is greater than the hybridomas in a culture after cell fusion. The cells secreted antibodies even after a short period. Since the multiplication of the transformed cells interferes with the multiplication of newly formed hybridomas, it is necessary to develop a countermeasure therefor.

SUMMARY OF THE INVENTION

An object of the invention is to provide a chicken cell capable of being used as a parental cell for production of a chicken monoclonal IgG antibody wherein hybridomas formed by fusing the cell multiply in precedent to others, especially the transformed cells.

The inventors investigated eagerly in order to achieve the above object, and have succeeded in obtaining a cell line which has achieved the object from the R27H cells by imparting a resistance to oaubain which is a specific inhibitor to $Na^+$, $K^+$—ATPase.

Thus, the present invention provides a thymidine kinase-lacking hybridoma having a resistance to ouabain and an Ig-producing ability in which a chicken B lymphoblast cell is fused with an immunized chicken spleen cell.

DETAILED DESCRIPTION OF THE INVENTION

Figure 1:
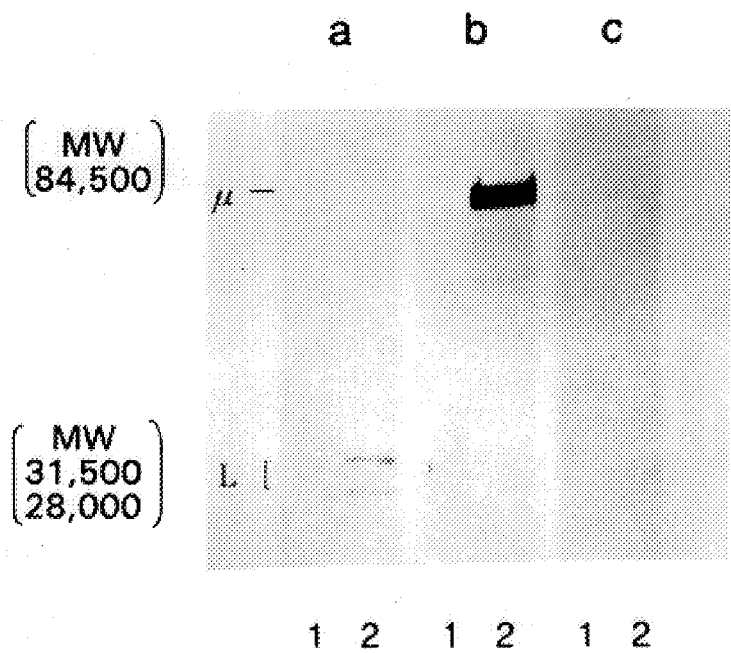
FIG. 1 shows developed color patterns of culture supernatant of cells of the invention subjected to electrophoresis followed by western blotting.

The cells of the invention can be obtained by culturing a thymidine kinase-lacking hybridoma having an Ig-producing ability and formed by fusing a chicken B lymphoblast cell with an immunized chicken spleen cell, in a culture medium containing ouabain, and isolating a hybridoma having resistance to ouabain.

The established thymidine kinase-lacking hybrid cell is obtained from chicken B lymphoblast. The kind of chicken is not limited, and for example, white leghorn, white rock and the like can be utilized.

The chicken B lymphoblast cell line is obtained from a chicken B lymphoblast cell suffering from cancer by a chicken retrovirus.

The B lymphoblast cell line having self proliferation potency thus obtained is mutated, and thymidine kinase-lacking cells are selected. The mutation may be conducted by a physical means, such as UV irradiation, or by utilizing an agent, such as ethyl methanesulfonic acid (EMS), nitroguanidine or ICR-191. The isolation of the thymidine kinase-lacking cell from the mutant cells may be conducted, for example, by culturing in a culture medium containing a thymidine analog, such as trifluorothymidine (TFT) or bromodeoxyuridine, and cloning. The culture medium may be a conventional medium for cell cultures, for example, RPMI 1640 medium, Dulbecco's modified MEM medium or the like to which 5–15% of fetal bovine serum (FBS) or the like is added. The culture conditions may also be similar to conventional cell culture conditions and, for example, may be at about 37°–41° C. in an atmosphere of air to which about 5–10% of $CO_2$ is added.

The established thymidine kinase-lacking cell thus obtained has a self proliferation potency, but it dies when cultured in a HAT medium. Besides, when it is measured by the indirect fluorescent antibody method, no cell synthesizes chicken Ig. This cell is designated as the HU3R cell.

The HU3R cell is fused with an immunized chicken spleen cell . The spleen cell may be prepared by injecting several times an antigen, such as inactivated Newcastle disease virus, together with an adjuvant, into a chicken, and excising it after breeding. The fusion is conducted by a known cell fusion technique, such as polyethylene glycol, electric fusion or PVJ virus.

The hybrid cell obtained is further mutated, and a thymidine kinase-lacking cell line is selected. It is preferable that these treatments are conducted after the subculture of the hybrid cell is continued until the growth becomes stable. The mutation treatment and the selection of thymidine kinase-lacking cells may be conducted similar to the aforementioned method. Besides, if necessary, mutation means and/or conditions may be changed. The production of Ig can be detected by detecting—$\gamma$ chains, $\mu$ chains and L chains which are a part of Ig, and the detection of these chains may be conducted according to a known method. For example, the indirect fluorescent antibody method using an anti-chicken Ig anti-$\gamma$ chain antibody and a fluorescein-labeled second antibody, flow cytometry, etc. can be utilized. The production of Ig can be confirmed by the confirmation of one of a $\gamma$ chain, $\mu$ chain or L chain.

The thymidine kinase-lacking cell has HAT sensitivity and Ig-producing ability. Examples of the cell are R27H1 (FERM BP-3475), R27H4 (FERM BP-3478), etc.

Subsequently, ouabain resistance is imparted to the cell. A means for imparting the ouabain resistance is to mutate the cell by a physical means, such as UV irradiation, or by using an agent, such as EMS, nitroguanidine or ICR-191, followed by cloning the mutant cells by culturing them in a medium containing ouabain. The culture medium may be a conventional medium for cell culture, for example, RPMI 1640 medium, Dulbecco's modified MEM medium or the like to which 5–15% of fetal bovine serum (FBS) or the like is added. It is preferable that the mutant cell is first cultured at an ouabain concentration of about $1\times10^{-7}$–$1\times10^{-5}$M, and the ouabain concentration elevated according to the multiplication of the cell. A suitable final concentration is about $5\times10^{-5}$–$5\times10^{-4}$M. The culture conditions may also be similar to those of conventional cell culturing, and, for example, may be at about 37°–41° C. in an atmosphere of air to which about 5–10% of $CO_2$ is added.

The ouabain-resistant cell is cultured in an HAT medium to confirm that all cells died completely after 5–6 days from the start of culturing. The expression of Ig can be confirmed by the indirect fluorescent antibody method using anti-chicken Ig antibody and fluorescein-labeled secondary antibody, or the like.

The established hybrid cell having Ig-producing ability thus obtained is further fused with an immunized chicken spleen cell. The immunization and the fusion may be similar to the aforementioned method. Since the antigen used for immunization is considered to impart IgG-producing ability to the cell after fusion with the immunized chicken spleen cell, the antigen is selected according to the desired IgG.

The IgG may be produced by culturing the hybrid cell similarly to the aforementioned method, and the IgG can be produced and accumulated in the culture supernatant by culturing for about 1–30 days. Separation of IgG may be conducted by utilizing a known means, such as affinity chromatography, gel filtration, ion exchange chromatography, ethanol fractionation, rivanol fractionation, PEG fractionation, etc.

According to the invention, specific antibody-producing cells can be obtained in a high efficiency by fusing a thymidine kinase-lacking ouabain-resistant cell line, e.g. MuH1 or MuH4, as a parental cell line, and growth of the specific antibody-producing cells is stable. Growth of retrovirus-transformed cells has not been found at all. The production of antibody is stable, and chicken IgG can be produced in quantity. The antibodies produced are monoclonal, and can be utilized not only in fundamental studies in chicken immunity but also as antibodies for medicines and clinical assay reagents.

EXAMPLE

I. Preparation of Ouabain-Resistant HAT-Sensitive Cell Line

I-1. Chicken Cell Line

R27H1 (FERM BP-3475) and R27H4 (FERM BP-3478) used in this example are parental cell lines established in previous studies. R27H1 and R27H4 were cultured in Iscove's modified Dulbecco's medium (IMDM) containing 10 $\mu$g/ml TFT and 10% FBS, placed in an incubator at 38.5° C. in an air atmosphere containing 5% $CO_2$, and subcultured for 2–4 days.

I-2. Preparation of Ouabain-Resistant cell 72.88 mg ouabain was dissolved in a phosphate buffer solution (PBS(–)) so as to become 20 ml ($5\times10^{-3}$M) and sterilized by a 0.45 $\mu$m sterilization filter. Then, the ouabain solution was put into sterilization tubes, and stored at 4° C. under dark conditions.

Mutation of R27H1 and R27H4 was carried out by suspending R27H1 cells or R27H4 cells in a RPMI 1640 medium containing 5% FBS in a concentration of $2\times10^5$ cells/ml, culturing at 38.5° C. in a 5% $CO_2$ incubator for 6 hours, adding EMS to the medium at a concentration of 600 $\mu$g/ml, and further culturing for 24 hours. After culturing, cells were washed three times with RPMI 1640 medium to remove EMS, and then further cultured by suspending them in a RPMI 1640 medium containing 10% FBS for the purpose of the expression of mutation.

After the mutated cells appeared from culturing 2–4 days, the cells were suspended in an IMDM medium containing $1\times10^{-5}$M ouabain and 10% FBS at a concentration of $1\times10^{-5}$ cells/ml, and 100 $\mu$l of cell suspension was put into a 96 well plate for tissue culture. After culturing at 38.5° C. in a 5% $CO_2$ incubator for several days, the grown cells were further allowed to grow in the same medium as mentioned above. When the multiplication became stable, the reagent concentration of the medium was gradually elevated to $1\times10^{-4}$M.

I-3. Cloning of Ouabain-Resistant Cells by Soft Agar Method

Cloning of the ouabain-resistant cells thus obtained was conducted by culturing on a soft agar medium containing $1\times10^4$M ouabain. After about two weeks culturing, colonies that grew very well on the soft agar were taken out and cultured in a growth medium containing $1\times10^{-4}$M ouabain, at 38.5° C. in a 5% $CO_2$ incubator, and particularly well grown clones were selected from the obtained clones. When the selected clones were cultured in a HAT medium containing $1\times10^{-4}$M hypoxanthine, $0.8\times10^{-7}$M aminopterin and, $1.6\times10^{-5}$M thymidine, all the cells were dead completely dead 5–6 days after the start of culturing. Accordingly, these clones could be used as a parental cell for cell fusion, and were designated as MuH1 (FERM BP-5442) and MuH4 (FERM BP-5443).

II. Properties of Ouabain-Resistant HAT-Sensitive Cell Lines

II-1. Sensitivity of Cell Lines Obtained by Cloning to HAT Medium

Sensitivity of the cell lines obtained by the cloning to HAT medium was examined. Cells to be tested were suspended in a RPMI 1640 medium containing 10% FBS at a concentration of $1\times10^5$ cells/ml, and 100 $\mu$l of cell suspension was put into each well of a 96 well plate for tissue culture. 100 $\mu$l of a RPMI1640 medium containing 10% FBS, $1\times10^{-4}$M hypoxantine, $1.6\times10^{-5}$ thymidine and $0.05-2\times10^{-7}$M aminopterin was added to each well, and cultured at 38.5° C. in a 5% $CO_2$ incubator. Cells in three wells of 96 well plate were recovered at the start, after 2, 4, 6, 8, 10 and 14 days, respectively, and a dead cell rate was determined.

II-2. Detection of Cytoplasmic Immunoglobulin (cIg) Expressing in Ouabain-Resistant Cell Line Expression of cIg in ouabain-resistant cell lines was examined by the indirect immunofluorescent method. Cells to be tested were transferred to a tube and washed three times with cold PBS (−). A small amount of a cell suspension in a high concentration was placed on a cover glass previously washed with ethanol and applied uniformly by a Pasteur pipette. After air-drying, the cover glass was put in a test tube, and a sufficient amount of an acid alcohol (acetic acid: ethanol=5:95) which was previously chilled to −20° C. was put into the test tube to fix the cells by leaving at −20° C. for 15 minutes. After air-drying, a suitable amount of rabbit anti-chicken L chain, rabbit anti-chicken $\mu$ chain and rabbit anti-chicken $\gamma$ chain diluted 50 times, 80 times and 60 times, respectively was placed on the cover glass as primary antibodies, and allowed to react at 37° C. for 2 hours or at 4° C. overnight in a moistened box. After the reaction was completed, the cells were washed 5 times with cold PBS (−). Fluorescein-labeled goat anti-rabbit IgG diluted 40 times was put as a secondary antibody, and allowed to react at 37° C. in a moistened box. After 1 hour, the cells were sufficiently washed, and then sealed by placing a solution prepared by mixing non-fluorescent glycerin and PBS (−) at a mixing ratio of 9:1 on the cover glass, and observed by a fluorescence microscope.

II-3. Measurement of Cell Growth Rate

The generation time of ouabain-resistant cells was measured. Cells to be tested were suspended in a RPMI 1640 medium containing 10% FBS at a concentration of $2\times10^5$ cell/ml. 1 ml of the cell suspension was put into each well of a 24 well plate for tissue culture, and cultured at 38.5° C. in a 5% $CO_2$ incubator. Cells from three wells were recovered every day and the number of living cells and dead cells were counted. Respective numeral values were plotted on a semilogarithmic paper from the start of culture to 1 week thereafter to prepare a growth curve. The generation time was calculated by the following formula.

Generation time; g is, $$g=(t_2-t_1)13.32\times\log(x_2/x_1)$$

$t_1$, $t_2$: time (hours)

$x_1$, $x_2$: number of living cells

II-4. Detection of Chicken Immunoglobulin

Chicken immunoglobulin in culture supernatants of ouabain-resistant cells was detected by the western blotting method. Ouabain-resistant cells to be tested were cultured in a serum-free IMDM medium for 24 hours, and the culture supernatant was added to 50% ammonium sulfate. Precipitates were collected and mixed with an electrophoresis buffer containing 2-mercaptoethanol (2-ME). The mixture was boiled at 100° C. for 3 minutes and used as the sample for electrophoresis. SDS polyacrylamide gel electrophoresis (SDS-PAGE) was conducted using 10% acrylamide gel. 3–5 $\mu$g of a sample was charged into each lane of a minislab gel, and allowed to migrate at 20–40 mA.

Thereafter, the migrants were transferred to a nitrocellulose membrane by the semidrying method, and color bands developed using antibodies were observed.

The antibody to chicken immunoglobulin used as the primary antibody above was prepared as follows. 250 $\mu$l of a PBS (−) solution. containing 100 $\mu$g chicken IgG or chicken IgM was mixed with an equal volume of FCA. A female Balb/c mouse was immunized by peritoneal injection, and then, further immunized with 125 $\mu$l of chicken IgM or IgG solution intravenously as a secondary immunization. Thereafter, the spleen cell was fused with mouse myeloma cell SP 2/0-Ag14 by a known cell fusion method, and the antibody was obtained by culturing the hybridoma. Thus, anti-chicken L chain (1:3000), anti-chicken $\gamma$ chain (1:3000) and anti-chicken $\mu$ chain (1:3000) mouse monoclonal antibodies (ascites) were prepared and used as the primary antibody, peroxidase (HRPO)-labeled goat anti-mouse IgG (1:300) was used as the secondary antibody, and dimethylaminobenzene (DAB) was used as the substrate.

II-5. Results

As to two clones of MuH1 and MuH4, expression of cIg was examined. As a result, expression of $\mu$ chain was found in MuH1, and expression of $\mu$ chain and L chain was found in MuH4, as shown in Table 1. Since chicken immunoglobulins appeared in the above two clones, in order to examine their producibility, chicken immunoglobulins in the culture supernatant of each cell were detected by the ELISA method and the western blotting method. As a result, secretion of $\mu$ chain and L chain were found in the culture supernatant of MuH4, but secretion of chicken immunoglobulin was not found in the culture supernatant of MuH1, as shown in FIG. 1. The generation times of both clones were longer than those of R27H1 and R27H4 by 2–3 hours (Table 1).

Figure 2:
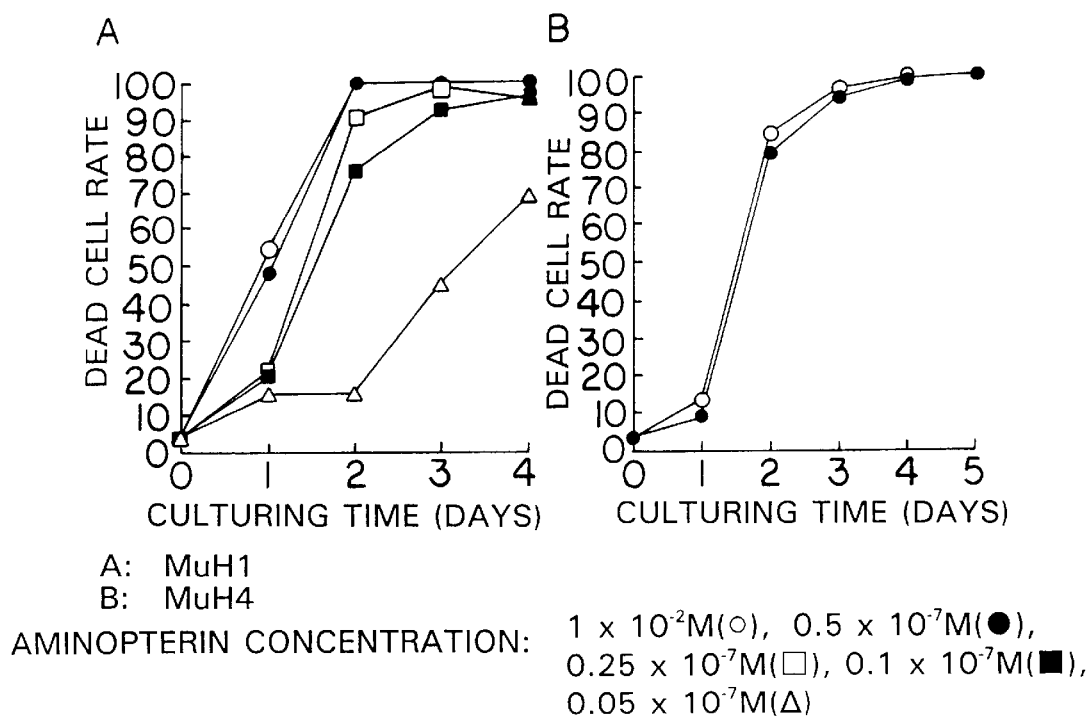
FIG. 2 is graphs illustrating the variation of the dead cell rate with time obtained by culturing cells of the invention with varying aminopterin concentration in an HAT medium.

Subsequently, sensitivities of MuH1 and MuH4 were examined to an aminopterin concentration of HAT medium. As shown by the results in FIG. 2, in $0.5\times10^{-7}$M aminopterin concentration, MuH4 cells were completely dead 5 days from the start of culturing, and MuH1 cells were completely dead 2 days from the start of culturing, respectively. Aminopterin sensitivity of MuH1 cells was further examined to a low concentration. As a result, about 95% of cells were dead 4 days from the start of culturing, but a part of cells grew, in a 0.25 or $0.1\times10^{-7}$M aminopterin concentration.

TABLE 1

Characteristics of Parental Cell Lines

| Cell Line | Ig Expression | | | | Generation Time (hr) |
|---|---|---|---|---|---|
| | Cytoplasmic Ig | | | | |
| | L | μ | γ | Secretion | |
| R27H1 | − | + | − | μ | 17.29 |
| R27H4 | + | + | − | IgM | 13.80 |
| MuH1 | − | + | − | ND* | 20.89 |
| MuH4 | + | + | − | IgM | 15.72 |

*Not detectable

III. Cell Fusion of Human IgG-Immunized Chicken Spleen Cell with MuH1, MuH4 as Patental Cell III-1. Immunized Chicken In the example, CB line white leghorn was used as the chicken for immunization.

III-2. Antigen, Immunization Schedule

Figure 3:
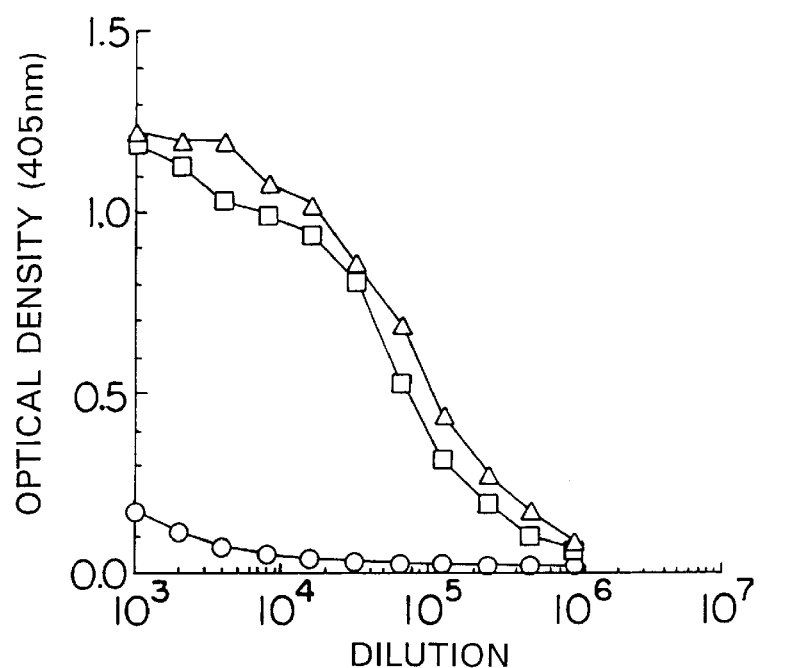
FIG. 3 is a graph showing titers of anti-human IgG sera produced by chicken, which was used to isolate spleen cells for the fusion with cells of the invention.

Human IgG was used as the antigen, and 200 μg/ml human IgG solution was prepared using PBS (−). Chickens of 4–6 weeks old were immunized intramuscularly with 100 μg of the human IgG in 500 μl PBS (−) emulsified with an equal volume of FCA. After 3–4 weeks from the primary immunization, the chickens were injected with 200 μg of human IgG intravenously as a secondary immunization. Titer of chicken serum after each immunization was measured by the ELISA method (FIG. 3).

III-3. Cell Fusion

A. Preparation of Medium

An IMDM medium containing 10% FBS was used as the medium for cell fusion. Hypoxantine, aminopterin and thymidine were added an IMDM medium containing 15% FBS at a concentration of $1 \times 10^{-4}$M, $2 \times 10^{-7}$M and $1.6 \times 10^{-5}$M, respectively, and used an HAT medium.

B. Preparation of Chicken Spleen Cell

The chicken were sufficiently phlebotomized by drawing blood from the heart, and the spleen was taken out. The spleen was decapsulated, and roughly crushed by a scissors. The crushed matter was put in a glass homogenizer wherein about 10 ml of serum-free RPMI 1640 medium was added and the homogenizer was run 2–3 times to prepare a cell suspension. The suspension was passed through a stainless steel screen (#200 mesh), and centrifuged at 273 G for 5 minutes. The supernatant was completely removed, and about 40 ml of serum-free RPMI 1640 medium was added to the cell precipitates. In order to remove erythrocytes from the cell suspension, about 4 ml of the cell suspension was gently superposed on about 2 ml of Ficoll-Paque placed in a 15 ml centrifuge tube, and centrifuged at 715 G for 10 minutes. After centrifugation, cells located between the supernatant and the Ficoll-Paque were taken out, and suspended in a suitable amount of serum-free RPMI 1640 medium. The suspension was washed three times by centrifugation to prepare a chicken spleen cell suspension.

C. Cell Fusion

Parental cells were recovered in a 50 ml polypropylene centrifuge tube, and washed three times with a serum-free RPMI 1640 medium. The washed parental cells were mixed with the antigen-immunized spleen cells at a mixing ratio of 1:5, and centrifuged at 267 G for 5 minutes. The supernatant was removed completely by suction and agglutination of cells was loosened by tapping the bottom of the centrifuge tube lightly. Then, 1 ml of PEG 1500 solution previously warmed to 38° C. was gradually added while taking 1 minute. Meanwhile, the centrifuge tube was shaken laterally, and the suspension was stirred occasionally by the tip of a pipette. After adding the PEG solution, 10 ml of serum-free RPMI 1640 medium previously warmed to 38° C. was added gradually while taking about 5 minutes. About 30 ml of the same medium was further added and centrifuged at 300 G for 5 minutes. The supernatant was gently removed by suction and the medium for hybridoma containing 10% FBS was added.

The cell precipitates were loosened lightly, and 100 μl (5 or $8 \times 10^5$ spleen cells/well) of the cell suspension was put into each well of a 96 well plate for tissue culture, and cultured at 38.5° C. in a 5% $CO_2$ incubator.

After 24 hours, 100 μl of an HAT medium doubled in concentration was added to each well, and after the second day after cell fusion, the medium was changed every 2–4 days to an HAT medium having a normal concentration. From the 10–14th day, the medium was changed to an HT medium, and cultured for 1 week. Cells in some wells in the plate were cultured using a medium containing $2 \times 10^{-5}$M ouabain 7 days after the fusion. Hypoxanthine, thymidine and aminopterin concentration of the HAT medium were $1 \times 10^{-4}$M, $1.6 \times 10^{-5}$M and $0.5$–$0.8 \times 10^{-7}$M, respectively.

As shown by the results in Table 2, cell growth was found in all wells using R27H4, and the cells grown in most wells were small cells, possibly not hybridomas.

In the case of MuH1, cells began to die the second day after HAT selection, and most cells were dead by the 4–5th day. On the other hand, in the case of MuH4, the cells first grew, but began to die by the 4th day, and most cells were dead by the 6–8th day. Hybridomas appeared in every well from about the 7–8th day, and the hybridomas grew stably. The fusion rate of MuH1 was 60.76% and 73.96% in the case of 5 or $8 \times 10^5$ spleen cells/well, and that of MuH4 was 20.49% and 17.36%, respectively. Growth, of small cells which were possibly not hybridomas was not found at all.

III-4. ELISA for Screening Hybridoma

In order to detect specific antibodies, 50 μl of human IgG, human IgG-Fc or human IgG-Fab diluted with PBS(−) at a concentration of 1 μg/ml was put into each well of an ELISA plate for ELISA, and immobilized by allowing it to react at 4° C. overnight. The ELISA plate was washed 5 times with PBS (−) containing 0.05% Tween-20 (Tween-PBS), and 200 μl of PBS (−) containing 1% gelatin was added to each well, followed by allowing it to react at 37° C. for 1 hour. After washing with Tween-PBS, 50 μl of the supernatant of the wells wherein hybridomas appeared was added to each wells of the plate. After allowing it to react at 37° C. for 2 hours, the plate was washed with Tween-PBS. 50 μl of HRPO-goat anti-chicken IgG (1:3000) diluted 3000 times with Tris buffer solution (TBS) was added to each well, and allowed to react at 37° C. for 1 hour. After washing with Tween-PBS, 100 μl of substrate solution containing phenylenediamine was added to each well, and allowed to react for 30 minutes at room temperature under dark conditions. 50 μl of 2M $H_2SO_4$ was added to each well to terminate the reaction. Then, the absorbance at 490 nm was measured.

III-5. Western Blotting for Detection of Specificity

Specificity of the culture supernatant of hybridomas which indicated positive by the ELISA method was examined by the western blotting method. Each sample was mixed with human IgG-Fc and human IgG-Fab and 2-ME buffer solution, and boiled at 100° C. for 5 minutes. 10% acrylamide gel was used for SDS-PAGE. 0.1 μg of human IgG-Fc and 0.3 μg of human IgG-Fab were applied to each lane of a minislab gel, and electrophoretic migration was conducted. The human IgG-Fc was previously purified by Protein G Sepharose 4 (Pharmacia) .

After the electrophoretic migration, migrants were transfered to a nitrocellulose membrane and allowed to react with the culture supernatant of each hybridoma, HRPO-goat anti-chicken IgG (1:3000) was used as the secondary antibody and then the color was developed by DAB. In addition, HRPO-goat anti-human IgG (1:3000) was allowed to react as a control.

III-6. Results of Screening Hybridoma

Hybridomas which produced specific antibodies were screened by the ELISA method. As shown in the results by Table 2, exhibition of hybridomas having antibody-producing ability was found in hybridomas derived from MuH1 and MuH4. The production of antibodies of the hybridomas was very stable and it was successful in obtaining clones having antibody-producing ability from all hybridomas subjected to cloning by the soft agar culture. The specificity of the antibodies produced by the clones was examined by the ELISA method and the western blotting method.

TABLE 2

Comparison of Fusion Rate among Parental Cell Lines

|  | Parental Cell Line | Number of Wells Exhibiting Cell Growing (%) | Number of Wells Exhibiting Specific Antibody (%) |
|---|---|---|---|
| Exp. 1 | R27H4 | 288/288 (100) | 1/288 (0.01) |
|  | MuH1 | 175/288 (60.76) | 7/175 (4.00) |
|  | MuH4 | 59/288 (20.49) | 2/59 (3.39) |
| Exp.2 | R27H4 | 288/288 (100) | 2/288 (0.01) |
|  | MuH1 | 213/288 (73.96) | 11/213 (5.16) |
|  | MuH4 | 50/288 (17.36) | 7/50 (14.00) |

TABLE 3

Specificities of Chicken Monoclonal Antibodies

| mAb | ELISA (O.D. 492 nm) | | | Western Blotting | |
|---|---|---|---|---|---|
|  | IgG | IgG-Fc | IgG-Fab | IgG-Fc | IgG-Fab |
| CHM1-HuIg1 | 0.407 | 0.043 | 0.502 | – | + |
| CHM1-HuIg2 | 0.407 | 0.467 | 0.031 | + | – |
| CHM1-HuIg3 | 0.419 | 0.504 | 0.029 | + | – |
| CHM1-HuIg4 | 0.467 | 0.438 | 0.092 | + | – |
| CHM4-HuIgl | 0.389 | 0.458 | 0.021 | + | – |
| CHM4-HuIg2 | 0.352 | 0.398 | 0.081 | + | – |
| CHM4-HuIg3 | 0.465 | 0.459 | 0.035 | + | – |
| CHM4-HuIg4 | 0.412 | 0.478 | 0.0026 | + | – |

Figure 4:
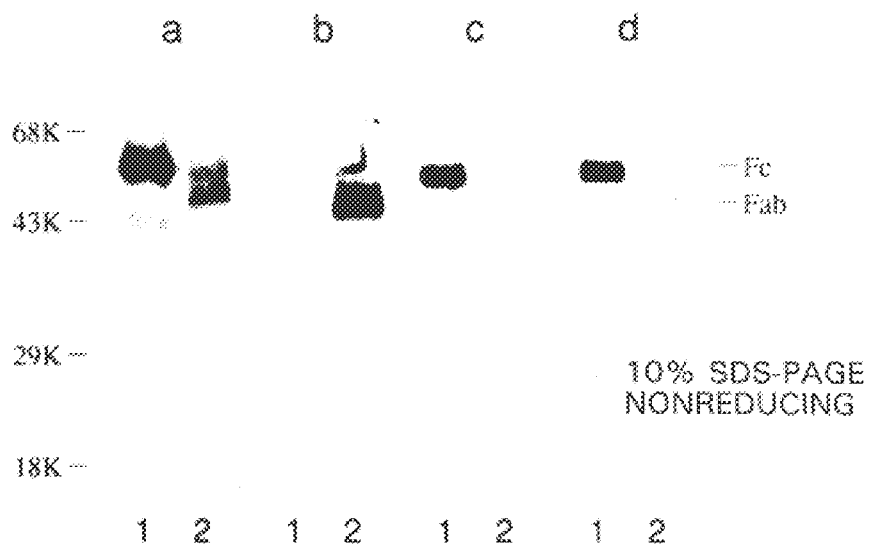
FIG. 4 shows developed color patterns of culture supernatant of cells formed by the hybrid cell of the invention with human IgG-immunized chicken spleen cell subjected to electrolysis followed by western blotting.

As shown in the results in Table 3, among the antibodies of the 8 hybridomas, 7 antibodies exhibited reactivity with human IgG-Fc, and the other antibody exhibited reactivity with human IgG-Fab. In the western blotting, all 7 antibodies, which exhibited reactivity with human IgG-Fc by the ELISA method, reacted with a 50 k daltons protein which is human IgG-Fc, but the reactivity with human IgG-Fab was not found. The other antibody (CHMI-HuIg1) reacted with human IgG-Fab (about 50 k daltons), but not with 50 k daltons protein of human IgG-Fc, and reacted with a molecular weight of 100 k daltons protein or more. Two antibodies (CHM1-HuIg3 and CHM4-HuIg1) which exhibited the reactivity with human IgG-Fc and the antibody (CHM1-HuIg1) which exhibited the reactivity with human IgG-Fab were subjected to western blotting, and the results were shown in FIG. 4.

IV. Properties of Hybridomas Fused by MuH1 or MuH4 Cells and Human IgG-Immunized Chicken Spleen Cells IV-1. ELISA for Detection of Specificity of Chicken Immuonogloblin Type Specificity of chicken immnoglobulin type was detected by the ELISA method. In order to detect the specificity of the antibodies, 50 µl of human IgG diluted with PBS(–) at a concentration of 1 µg/ml was put into each well of a ELISA plate, and immobilized by allowing it to react at 4° C. for 1 day. After allowing a culture supernatant of each hybridoma to react, the aforementioned anti-chicken L chain (1:5000), anti-chicken γ chain (1:50000) and anti-chicken µ chain (1:50000) mouse monoclonal antibodies (ascites) were used as the secondary antibodies, and then, HRPO-goat anti-mouse IgG (1:3000) was used as the tertiary antibody.

IV-2. Reactivity with Human IgG

As to chicken anti-human IgG antibodies produced by 8 hybridomas derived from MuH1 or MuH4, their types of chicken immunoglobulins were examined by the ELISA method. As shown by the results in Table 4, all antibodies having γ chains and L chains produced by the 8 clones exhibited reactivity with human IgG, but the antibody having µ chains did not exhibit reactivity with human IgG at all.

TABLE 4

Comparison of Ig Type of Antibodies Produced by Hybridomas

| Hybridoma | ELISA (O.D. 492 m) | | |
|---|---|---|---|
|  | Anti L Chain | Anti γ Chain | Anti µ Chain |
| CHM1-HuIg1 | 0.68 | 0.892 | –0.011 |
| CHM1-HuIg2 | 0.712 | 0.861 | –0.003 |
| CHM1-HuIg3 | 0.703 | 0.842 | –0.009 |
| CHM1-HuIg4 | 0.544 | 0.769 | –0.011 |
| CHM4-HuIgl | 0.502 | 0.632 | –0.014 |
| CHM4-HuIg2 | 0.354 | 0.525 | 0.017 |
| CHM4-HuIg3 | 0.672 | 0.694 | –0.015 |
| CHM4-HuIg4 | 0.397 | 0.655 | –0.013 |

IV-3. ELISA for Quantification of Chicken Monoclonal Antibodies

The concentration of immunoglobulin secreted from the hybridomas was determined by the ELISA method. Each culture supernatant to be tested was prepared by culturing antibody-producing hybridoma cells in an IMDM medium containing 10% FBS and $5 \times 10^{-5}$M or no ouabain in a concentration of $5 \times 10^5$ cells/ml, and then culturing at 38.5° C. for 24 hours in a 5% $CO_2$ incubator.

On the ELISA plate, goat anti-chicken IgM-Fc (1:500, 50 µl/well) was immobilized for the measurement of the concentration of chicken IgM or goat anti-chicken IgG-Fc (1:500, 50 µl/well) was immobilized for the measurement of the concentration of chicken IgG. After blocking by Block Ace, the ELISA plate was allowed to react with 50 µl of each hybridoma culture supernatant (dilution ratio, 1:10~1:1280) and chicken IgM (50 µl/well) or chicken IgG (50 µl/well) diluted with PBS (–) to 1–300 ng/ml as a control. The aforementioned anti-chicken µ chain (1:100,000) and anti-chicken γ chain (1:10,000) mouse monoclonal antibodies were used as the secondary antibodies, and HfRPO-goat anti-mouse IgG (1:3,000) was used as the tertiary antibody.

IV-4. Quantification of Immunoglobulins in Chicken Hybridomas Culture

The quantification of immunoglobulins in chicken hybridomas culture was examined by the ELISA method. Hybridomas stably growing in a medium containing ouabain were used for the examination of antibody-producing ability in the medium containing ouabain. As shown by the results in Table 5, although the concentration of immunoglobulin was decreased in the medium containing ouabain compared with an ouabain-free medium, the decrease was not so remarkable in most hybridomas. The concentration of immunoglobulin of MuH1-derived hybridomas was greater than MuH4-derived hybridomas. The concentration of IgG from MuH4-derived hybridomas was less than 1 μg/ml, but 3 hybridomas among 4 MuH1-derived hybridomas produced more than 2 μg/ml IgG under ouabain-free conditions. Particularly, CHM1-HuIg 3, which did not express a μ chain, produced IgG in a great amount of more than 5 μg/ml. On the other hand, the concentration of IgM from MuH1-derived hybridomas was similar to the concentration of IgG, but the concentration of IgM from MuH4-derived hybridomas was 1–4 times as much as the concentration of IgG.

TABLE 5

Concentration of IgG and IgM Produced by Parental Cells and Their Hybridomas

| | IgG (μg/ml) | | IgM (μg/ml) | |
|---|---|---|---|---|
| Cell Line | No Oua Added | Oua Added | No Oua Added | Oua Added |
| MuH1 | 0 | 0 | 0 | 0 |
| MuH4 | 0 | NT* | 0.26 | NT |
| CHM1-HuIg1 | 2.38 | 1.58 | 3.12 | 2.07 |
| CHM1-HuIg2 | 3.96 | 3.48 | 3.18 | 2.4 |
| CHM1-HuIg3 | 5.22 | 5.92 | 0 | 0 |
| CHM1-HuIg4 | 0.24 | 0.19 | 0.26 | 0.26 |
| CHM4-HuIg1 | 0.72 | 0.57 | 1.53 | 1.2 |
| CHM4-HuIg2 | 0.45 | 0.31 | 1.98 | 1.47 |
| CHM4-HuIg3 | 0.65 | 0.26 | 0.78 | 0.76 |
| CHM4-HuIg4 | 0.75 | 0.27 | 2.07 | 0.29 |

*Not tested

We claim:

1. A method of preparing a thymidine kinase-deficient hybridoma having a resistance to ouabain and an Ig-producing ability comprising the steps:
   (a) mutating a chicken B lymphoblast cell line to produce a thymidine kinase-deficient cell;
   (b) isolating a thymidine kinase-deficient chicken B lymphoblast cell;
   (c) fusing the isolated thymidine kinase-deficient chicken B lymphoblast cell with an immunized chicken spleen cell to produce a fusion cell;
   (d) mutating the fusion cell to produce a thymidine kinase-deficient fusion cell having HAT sensitivity and Ig-producing ability;
   (e) isolating a thymidine kinase-deficient fusion cell having HAT sensitivity and Ig-producing ability;
   (f) mutating the thymidine kinase-deficient fusion cell having HAT sensitivity and Ig-producing ability to produce a mutant cell having a resistance to ouabain;
   (g) culturing said mutant cell in a culture medium containing ouabain;
   (h) recovering a thymidine kinase-deficient hybridoma having a resistance to ouabain and an Ig-producing ability.

2. A thymidine kinase-deficient hybridoma having a resistance to ouabain and an Ig-producing ability, said hybridoma being produced by a process in which a chicken B lymphoblast cell is fused with an immunized chicken spleen cell, wherein said hybridoma is MuH1 (FERM BP-5442) or MuH4 (FERM BP-5443).

3. A method of producing antibodies comprising the steps of:
   (a) mutating a chicken B lymphoblast cell line to produce a thymidine kinase-deficient cell;
   (b) isolating a thymidine kinase-deficient chicken B lymphoblast cell;
   (c) fusing the isolated thymidine kinase-deficient chicken B lymphoblast cell with a first immunized chicken spleen cell to produce a fusion cell;
   (d) mutating the fusion cell to produce a thymidine kinase-deficient fusion cell having HAT sensitivity and Ig-producing ability;
   (e) isolating a thymidine kinase-deficient fusion cell having HAT sensitivity and Ig-producing ability;
   (f) mutating the thymidine kinase-deficient fusion cell having HAT sensitivity and Ig-producing ability to produce a mutant cell having a resistance to ouabain;
   (g) culturing said mutant cell in a culture medium containing ouabain;
   (h) recovering a thymidine kinase-deficient hybridoma having a resistance to ouabain and an Ig-producing ability;
   (I) fusing the thymidine kinase-deficient hybridoma having resistance to ouabain with a second immunized chicken spleen cell to produce a product hybridoma with IgG-producing capability;
   (j) isolating said product hybridoma producing an IgG monoclonal antibody; and
   (k) producing antibodies from said product hybridoma producing an IgG monoclonal antibody.

4. The method of claim 3 wherein said thymidine kinase-deficient hybridoma is MuH1 (FERM BP-5442) or MuH4 (FERM BP-5443).

* * * * *